United States Patent
Enzelberger

(10) Patent No.: US 9,267,952 B2
(45) Date of Patent: Feb. 23, 2016

(54) DECONVOLUTION METHOD

(75) Inventor: Markus Enzelberger, Planegg (DE)

(73) Assignee: MorphoSys AG, Martinsried (DE)

( * ) Notice: Subject to any disclaimer, the term of this patent is extended or adjusted under 35 U.S.C. 154(b) by 730 days.

(21) Appl. No.: 13/124,127

(22) PCT Filed: Nov. 4, 2009

(86) PCT No.: PCT/EP2009/064625
§ 371 (c)(1),
(2), (4) Date: Apr. 14, 2011

(87) PCT Pub. No.: WO2010/052244
PCT Pub. Date: May 14, 2010

(65) Prior Publication Data
US 2011/0200589 A1    Aug. 18, 2011

Related U.S. Application Data

(60) Provisional application No. 61/111,510, filed on Nov. 5, 2008, provisional application No. 61/150,817, filed on Feb. 9, 2009.

(51) Int. Cl.
C40B 30/04    (2006.01)
G01N 33/68    (2006.01)

(52) U.S. Cl.
CPC ............ *G01N 33/6845* (2013.01); *C40B 30/04* (2013.01)

(58) Field of Classification Search
None
See application file for complete search history.

(56) References Cited

U.S. PATENT DOCUMENTS 5,811,238 A  *  9/1998  Stemmer et al. .................. 506/1
2004/0001849 A1*  1/2004  Punnonen et al. ......... 424/186.1

FOREIGN PATENT DOCUMENTS

| DE | 199 36 563 | 2/2001 |
| WO | WO91/14452 | 10/1991 |
| WO | WO95/31723 | 11/1995 |
| WO | WO97/22617 | 6/1997 |
| WO | WO97/42216 | 11/1997 |
| WO | WO01/02554 | 1/2001 |
| WO | WO01/25492 | 4/2001 |
| WO | WO2007/030771 | 3/2007 |
| WO | PCT/EP2009/064625 | 11/2009 |

OTHER PUBLICATIONS

Grothaus M. C. et al: "Selection of an immunogenic peptide mimic of the capsular polysaccharide of Neisseria meningitidis serogroup A using a peptide display library"; Vaccine, Butterworth Scientific Guildford, GB, vol. 18, No. 13, Jan. 18, 2000, pp. 1253-1263.

Xu W et al: "Passive immunization with human neutralizing monoclonal antibodies: correlates of protective immunity against HIV"; Vaccine, Butterworth Scientific Guildford, GB; vol. 20, No. 15, May 6, 2002, pp. 1956-1960.

John Haurum, CSO, Symphogen, Synergy of anti-EGFR antibody combination leading to superior anti-cancer efficacy, slides.

* cited by examiner

*Primary Examiner* — Christian Boesen
(74) *Attorney, Agent, or Firm* — Paul F. Wiegel

(57) ABSTRACT

The present invention relates generally to novel applications in combating infectious disease, cancer, allergy and autoimmune diseases. In one aspect, the invention relates to identifying one or more protein binding moieties of interest. In another aspect, the present invention relates to identifying one or more candidate vaccines.

8 Claims, No Drawings

DECONVOLUTION METHOD

CROSS-REFERENCE TO RELATED APPLICATION

This application claims the benefit of U.S. provisional application Ser. No. 61/150,817 filed Feb. 9, 2009 and U.S. provisional application Ser. No. 61/111,510 filed Nov. 5, 2008, which are both incorporated by reference in their entireties.

BACKGROUND OF THE INVENTION

Various therapeutics have been devised to combat diseases, such as, infectious disease, cancer, allergy and autoimmune diseases. Such therapeutics include antibiotics, vaccines and other biological-based agents, such as protein binding moieties, including antibodies. Antibodies, in particular, have shown great potential in combatting various pathogens, cancer, allergy and autoimmune diseases. Against pathogens, however, pathogen resistance, commonly referred to as antigen escape, currently remains a challenge. Antibodies, by their inherent specificity for a particular epitope of an immunogen, play an effective role in elucidating which epitope(s) are well suited for designing a regimen to attack the disease, whether through an antibody-based prophylactic or therapeutic, or a vaccine-based prophylactic or therapeutic based on such epitope(s). Thus, there remains a need to efficiently identify an ideal protein binding moiety or group of protein binding moieties, such as an antibody, for the treatment of such diseases. Specifically, there remains a need to efficiently identify an ideal protein binding moiety or group of protein binding moieties, such as an antibody, that can withstand pathogen resistance. Further, there remains a need to efficiently identify relevant epitopes for the design of effective vaccines.

Once immunogens believed to have therapeutic relevance are identified, protein binding moieties specific for the immunogen can be selected by screening libraries of protein binding moieties against one or more of the immunogens. A problem arising after the initial selection process, however, is that a large number of binders, often hundreds are identified. Each protein binding moiety typically has some relative specificity for the immunogen, but it is not known which of the plurality of binders has therapeutic utility, such as, efficacy against disease. One option, would be to tediously test each individual protein binding moiety for a desired property, but this would be an expensive and time consuming task. Embodiments of the present invention provide solutions to this problem.

Further, once immunogens are identified, vaccines can be generated. A problem in identifying vaccines, however, is the efficient selection of suitable component epitopes of interest. Embodiments of the present invention provide a solution to this problem.

These and other needs are satisfied by the present invention.

SUMMARY OF THE INVENTION

The present invention relates generally to novel applications in combating infectious disease, cancer, allergy and autoimmune diseases. In one aspect, the invention relates to efficiently identifying one or more protein binding moieties, such as an antibody, having efficacy against disease. In another aspect, the present invention relates to efficiently identifying one or more candidate vaccines, especially multivalent vaccines, comprising of therapeutically relevant component epitopes.

In one aspect, the present invention provides methods of efficiently identifying a therapeutic agent, for example, a protein binding moiety or combinations of protein binding moieties efficacious against disease. After initial screening of a library comprising protein binding moieties against one or more immunogens, often large numbers of binders are identified each having some relative specificity for the immunogen, but it is not known which binders are efficacious against disease, i.e. are functional in assay or have in vivo efficacy. Embodiments of the present invention provide methods of efficiently identifying protein binding moieties efficacious against disease, thus excluding the protein binding moieties having specificity but not efficacy from further consideration.

Embodiments of the present invention provide a method for identifying a therapeutic agent comprising screening a library of protein binding moieties against an immunogen, obtaining a plurality of protein binding moieties specific for the immunogen, dividing the plurality into at least two pools, a first pool and a second pool, and testing one or both pools to determine efficacy against disease. Generally, each pool will contain at least one protein binding moiety that is unique to that pool, wherein each of the protein binding moieties in their respective pool are testable with the other protein binding moieties within said pool.

If efficacy against disease, for example, function in assay or in vivo, is observed in the first pool, but the second pool shows no efficacy then the protein binding moieties contained in the second pool can be quickly disqualified from further consideration. Therefore, this method rapidly narrows down the number of binders that are further tested. If the first pool shows efficacy, this means that at least one of the binders in the pool has functional activity.

Embodiments of the present invention provide a method wherein the first pool to the extent that efficacy against disease is observed in the first pool, is subsequently divided into two or more sub-pools, and the resulting sub-pools are tested for efficacy against disease. This subsequent step allows the further inclusion of functional binders and/or the further disqualification of a pool or sub-pool of binders. Such a method allows the rapid identification of functional binders, and the rapid exclusion of non-functional binders. This method may be repeated until all of the protein binding moieties, whether one or more, that are efficacious against disease are identified.

Embodiments of the present invention provide a method wherein the second pool is tested for efficacy against disease. Embodiments of the present invention provide a method wherein the second pool is divided into two or more sub-pools, to the extent that efficacy against disease is observed in the second pool, the resulting sub-pools are tested for efficacy against disease, and the one or more protein binding moieties that are efficacious against disease are identified.

Embodiments of the present invention provide a method for efficiently identifying binders having efficacy against disease, wherein efficacy is determined by function in vivo. In particular, the step of testing said protein binding moieties includes testing in vivo, for example, in a mouse model.

Embodiments of the present invention provide a method wherein the library of protein binding moieties used to screen against at least one immunogen comprises a phage display library. Further embodiments comprise a method wherein the phage display library displays antibodies or functional fragments thereof.

In another aspect, the present invention provides a pharmaceutical composition comprising the one or more protein binding moieties identified as efficacious against disease.

In another aspect, the present invention provides methods for efficiently elucidating polypeptide sequences that are particularly suited for formulating a vaccine. Preferably, the polypeptide sequences identified comprise multiple epitopes, thus, formulating a multivalent vaccine. Embodiments of the present invention further comprise mapping the epitopes of the immunogen bound by the protein binding moieties having efficacy against disease. Once the epitopes of the immunogen are identified they can be used in the production of vaccines comprising the one or more epitopes bound by the one or more protein binding moieties having efficacy against disease.

In another aspect, the present invention provides a method further comprising combining the protein binding moieties identified as efficacious against disease, testing the combination of protein binding moieties for efficacy against disease and identifying the synergistic combination of protein binding moieties. This aspect of the invention provides an efficient method for identifying synergistic combinations of protein binding moieties.

In another aspect, the present invention provides a pharmaceutical composition comprising the synergistic combination of protein binding moieties.

In another aspect, the present invention provides a vaccine comprising the epitopes of the immunogen that are specifically bound by the synergistic combination of protein binding moieties.

In another aspect, the present invention provides a method further comprising combining a subset of the protein binding moieties identified as a synergistic combination, wherein the subset combination comprises at least one less protein binding moiety than the synergistic combination, testing the subset combination of protein binding moieties for efficacy against disease, and identifying the subset combination of protein binding moieties that maintains synergistic activity.

In another aspect, the present invention provides a pharmaceutical composition comprising the subset combination of protein binding moieties that maintains synergistic activity.

In another aspect, the present invention provides a vaccine comprising the epitopes of the
immunogen that are specifically bound by the subset combination of protein binding moieties that maintains synergistic activity.

In another aspect, the present invention provides a method further comprising the screening of a library of protein binding moieties against a more than one antigen, for example, a first and a second immunogen.

In another aspect, the present invention provides a method wherein the step of obtaining a plurality of protein binding moieties that are specific for the immunogen further comprises:

combining the plurality of protein binding moieties specific for the first immunogen with the plurality of protein binding moieties specific for the second immunogen, testing the combination of pluralities of protein binding moieties for efficacy against disease, and identifying the synergistic combination of pluralities of protein binding moieties efficacious against disease.

In another aspect, the present invention provides a method further comprising identifying the synergistic combination of immunogens relevant for the treatment of disease.

In another aspect, the present invention provides a pharmaceutical composition, comprising the synergistic combination of pluralities of protein binding moieties specific for the one or more immunogens.

In another aspect, the present invention provides a vaccine, comprising the epitopes of the one or more immunogens that are specifically bound by the synergistic combination of pluralities of protein binding moieties identified.

In another aspect, the present invention provides a vaccine, comprising the synergistic combination of immunogens identified.

In another aspect, the present invention provides a method further comprising: combining a subset of the pluralities of protein binding moieties identified as a synergistic combination, wherein the subset combination comprises at least one less plurality of protein binding moieties than the synergistic combination; testing the subset combination of pluralities of protein binding moieties for efficacy against disease; and identifying the subset combination of pluralities of protein binding moieties that maintains synergistic activity.

In another aspect, the present invention provides a method further comprising: identifying the subset combination of immunogens relevant for the treatment of disease.

In another aspect, the present invention provides a vaccine, comprising the subset combination of immunogens identified.

In another aspect, the present invention provides a method for identifying a vaccine comprising the steps of: screening a library of protein binding moieties against a first and a second immunogen; obtaining a plurality of protein binding moieties that are specific for the first and second immunogens; combining the plurality of protein binding moieties specific for the first immunogen with the plurality of protein binding moieties specific for the second immunogen, testing the combination of pluralities of protein binding moieties for efficacy against disease; identifying the synergistic combination of pluralities of protein binding moieties efficacious against disease; and identifying the synergistic combination immunogens relevant for the treatment of disease.

In another aspect, the present invention provides a method further comprising manufacturing a vaccine comprising the immunogens identified as relevant for the treatment of disease.

DETAILED DESCRIPTION OF THE INVENTION

Definitions

A "therapeutic agent" includes, but is not limited to, any protein binding moiety capable of treating disease, including antibodies, which act as passive immunization. A therapeutic agent also includes vaccines, or multivalent vaccines which act as active immunization. Vaccines can contain dead or inactivated organisms, inactivated toxins produced by virulent pathogens, or peptides, such as, surface proteins of a pathogen. A therapeutic agent includes prophylactic utility.

A "protein binding moiety" includes, but is not limited to, backbones, otherwise known as scaffolds with a modified binding site; and antibodies, or functional fragments thereof. Scaffolds may be non-antibody alternatives that are useful because of a beneficial property, such as, stable structure, smaller size, or longer half life. Scaffolds include proteins comprising fibronectin binding domains, adinectin, anticalins, designed AR proteins (DARPins), T cell receptors, proteins comprising protein A domains, protein Z domains or Kunitz domains, Affibodys, ectoins, GFPs, cytochrome b562, proteins of the Knottin family, gamma-crystallin and ubiquitin. Antibodies, or functional fragments thereof, include Fabs, scFvs and other functional fragments. Protein binding moieties can generally be specific for any immunogen.

A "library" includes, but is not limited to, phage display, ribosomal display, bacterial display, yeast display and mammalian display libraries. A preferred embodiment of the present invention utilizes a phage display library, even though any library of protein binding moieties may be used. An example of a phage display library is a HuCAL® library, preferably the HuCAL GOLD® library, or more preferably the HuCAL Platinum® library. HuCAL GOLD® and Platinum® are Fab libraries based upon the HuCAL concept (Knappik et al., 2000; Krebs et al., 2001), in which all six CDRs are diversified, and which employs the CysDisplay® technology for linking Fab fragments to the phage surface (Lohning, 2001). A benefit of using a phage display library is that the genotype and phenotype are linked; therefore, the DNA encoding the antibodies or functional fragments thereof identified by the methods of the present invention can be readily identified. This allows for efficient reproduction of the identified antibodies or functional fragments.

An "immunogen" is a substance that stimulates the adaptive immune system, thus, when isolated can be used as a vaccine in active immunization. An immunogen can also be a target for therapeutic antibodies, which act in passive immunization. An immunogen may be an antigen. An immunogen includes a pathogen or other infectious agent that can cause disease or illness in a host. An immunogen may be a protein or a peptide or may even be a non-peptide entity, such as a sugar moiety or lipid. For the purposes of generating therapeutic antibodies, an immunogen is preferably a cell surface antigen, but may be any other type of antigen, including a soluble protein. An immunogen comprises at least one epitope or immunogenic determinant. An immunogen may also contain several epitopes or immunogenic determinants. The epitope comprises the specific amino acid residues that are bound by a single protein binding moiety. An epitope can be linear, conformational or discontinuous. An epitope can also be defined as the specific amino acids that protein binding moieties can be generated against. Either immunogens or individual epitopes of immunogens can be identified and subsequently used as vaccines.

"Synergistic" means a combination that is more effective than the sum of its individual components. For example, two protein binding moieties are synergistic if in combination they have a functional activity that is greater than the sum of their individual activities. Synergistic also means that a combination may only be as effective as the individual components, but because of the ability of the combination of protein binding moieties to bind to more than one immunogen or epitope of an immunogen, the combination may have a longer duration of effect or more consistent results than its individual components. For example, if a pathogen mutates and loses an immunogen, or becomes resistant to treatment against a certain immunogen, the combination of protein binding moieties may maintain its efficacy.

A combination of immunogens may also be considered synergistic, meaning that the combination of immunogens, when used as a vaccine generates a synergistic immune response, or when used as a target to generate protein binding moieties, the protein binding moieties specific for the combination of immunogens have a synergistic efficacy against disease.

"Efficacy against disease" means functional activity. Functional activity can be determined in vitro or in vivo in animals, including mammals, which preferably are humans. Efficacy against disease includes the inhibition of the virulence of a pathogen. Efficacy against disease would not include a protein binding moiety that merely has a relative specificity for an immunogen, as a protein binding moiety exhibiting efficacy against disease must also demonstrate efficacy against an immunogen. The quantity of functional activity or measure of efficacy, in order to be efficacious against disease, is case specific and can be determined by one of skill in the art.

"Testing" includes, but is not limited to in vitro and in vivo.

A "subset combination" is at least one less protein binding moiety or plurality of protein binding moieties than present in a combination of protein binding moieties or combination of pluralities of protein binding moieties.

"Relevant for the treatment of disease" means an immunogen that may be a target for protein binding moieties in the treatment of disease, or an immunogen that may act as a vaccine in the treatment or prophylaxis of disease.

The methods of the present invention are applicable within the areas of infectious disease, cancer, allergy and autoimmune diseases, in that they can be used to identify protein binding moieties efficacious against each of these diseases, and vaccines useful in the treatment or prophylaxis of each of these diseases.

The methods disclosed do not depend upon the specific method being used to identify the immunogens. Immunogens that are identified by any method known in the art can be used in the present methods.

Deconvolution After Screening Against One or More Immunogens

An embodiment comprises a method for efficiently identifying therapeutic agents efficacious against disease. For example, a library of protein binding moieties is screened against an immunogen. The result of the screening is a large plurality of protein binding moieties each having a relative affinity for the immunogen. A plurality may contain up to one hundred protein binding moieties or greater. Therefore, the time and effort required, in order to, individually test each protein binding moiety for functional activity against disease would be substantial.

An embodiment of the present invention provides a solution to this problem comprising a method for identifying a therapeutic agent efficacious against disease, comprising screening a library of protein binding moieties against at least one immunogen; obtaining a plurality of protein binding moieties that are specific for the immunogen; dividing the plurality of protein binding moieties into at least a first pool and a second pool, wherein each pool contains at least one protein binding moiety that is unique to that pool, and wherein the protein binding moieties in their respective pool are testable with the other protein binding moieties within said pool; testing said protein binding moieties from said first pool for efficacy against disease; dividing the protein binding moieties from said first pool into two or more sub-pools, to the extent efficacy against disease is observed, wherein each sub-pool contains at least one protein binding moiety; testing said protein binding moieties from said first and second sub-pools of said first pool for efficacy against disease; and identifying one or more protein binding moieties that are efficacious against disease. This method could be considered a method of deconvolution.

Preferably, the first and second pool will each contain at least two protein binding moieties. More preferably, the pools will each contain more than five protein binding moieties. Even more preferably, the pools will contain more than ten protein binding moieties. The larger the pools the more efficiently protein binding moieties lacking efficacy against disease can be disqualified from further study. Larger pools, therefore, result in a more efficient identification of protein binding moieties having efficacy against disease.

Another embodiment further comprises testing said protein binding moieties from said second pool for efficacy against disease; dividing the protein binding moieties from said second pool into two or more sub-pools, to the extent efficacy against disease is observed, wherein each sub-pool contains at least one protein binding moiety; testing said protein binding moieties from said first and second sub-pools of said second pool for efficacy against disease; and identifying one or more protein binding moieties that are efficacious against disease.

An embodiment of the present invention comprises a method for identifying therapeutic agents efficacious against disease, wherein a library is screened against one immunogen.

An embodiment of the present invention exemplifies a method for identifying protein binding moieties efficacious against disease, wherein a library is screened against one immunogen.

An embodiment of the present invention comprises a method for identifying therapeutic agents efficacious against disease, wherein the screening of a library of protein binding moieties comprises screening a library of protein binding moieties against two or more antigens.

An embodiment of the present invention exemplifies a method for identifying protein binding moieties efficacious against disease, wherein the screening of a library of protein binding moieties comprises screening a library of protein binding moieties against two or more antigens.

An embodiment can use one library or a plurality of libraries to screen against the two or more antigens.

Another embodiment comprises a method for identifying protein binding moieties efficacious against disease, comprising the steps of: (a) screening a library of protein binding moieties against an antigen; (b) obtaining a plurality of protein binding moieties that are specific for the antigen; (c) dividing the plurality of protein binding moieties into at least a first pool and a second pool, wherein each pool contains one or more protein binding moieties, and wherein the protein binding moieties in their respective pool are testable with the other protein binding moieties within said pool; (d) testing said protein binding moieties from said first pool for efficacy against disease; (e) dividing the protein binding moieties from said first pool into two or more sub-pools, to the extent inhibition of virulence of said pathogen is observed in step (d), wherein each sub-pool contains one or more protein binding moieties; (f) testing said protein binding moieties from said first and second sub-pools of said first pool for efficacy against disease; and (g) identifying one or more protein binding moieties from step (f) that are efficacious against disease.

Another embodiment comprises a method for identifying protein binding moieties efficacious against disease, further comprising the steps of: (h) testing said protein binding moieties from said second pool for efficacy against disease; (i) dividing the protein binding moieties from said second pool into two or more sub-pools, to the extent inhibition of virulence of said pathogen is observed in step (h), wherein each sub-pool contains one or more protein binding moieties; (j) testing said protein binding moieties from said first and second sub-pools of said second pool for efficacy against disease; and (k) identifying one or more protein binding moieties from step (j) that is efficacious against disease.

Another embodiment comprises screening with a phage display library displaying antibodies or functional fragments thereof. Antibodies or functional fragments thereof include, but are not limited to, scFvs, Fabs, Vhs, Vls, and IgGs.

Another embodiment further comprises converting the plurality of protein binding moieties specific for the immunogen obtained by the present method into full length IgGs prior to dividing and testing for efficacy against disease. For example, if the screening of immunogens is completed using a Fab library, or other functional fragment library, a conversion of the fragments obtained into full-length IgGs is preferable prior to testing as a test of full-length IgGs is more predictive of how therapeutic antibodies will perform during treatment in humans.

The protein binding moieties having efficacy against disease can be used to manufacture a pharmaceutical composition useful in therapeutic treatment against disease.

Another embodiment comprises a pharmaceutical composition comprising one or more of the protein binding moieties identified as efficacious against disease.

Once protein binding moieties efficacious against disease are identified, the epitopes of the immunogens that are specifically bound by the protein binding moieties can be mapped. These epitopes can then be generated and used as a multivalent vaccine. Another embodiment further comprises the steps of identifying one or more epitopes of the immunogen that are specifically bound by the one or more protein binding moieties identified as efficacious against disease; and manufacturing the one or more epitopes of the immunogen to form a multivalent vaccine.

Another embodiment comprises a vaccine, comprising one or more of the epitopes of the immunogen that are specifically bound by the one or more protein binding moieties identified as efficacious against disease.

It is contemplated that only one protein binding moiety efficacious against disease is identified. In that instance, the single epitope of the immunogen specifically bound by the protein binding moiety may be manufactured to form a vaccine.

It is also contemplated that no single antibody is discovered to have efficacy against disease. In that instance, then the results of the previous tests may be used to identify combinations of protein binding moieties efficacious against disease. To the extent that at least one of the above pluralities, pools or sub-pools showed efficacy against disease in testing.

An embodiment of the present invention can be applied to the area of infectious disease, wherein an embodiment comprises a method of identifying antibodies or functional fragments thereof that inhibit the virulence of a pathogen.

Synergistic Combinations of Protein Binding Moieties

A preferred embodiment comprises a method for identifying a synergistic combination of protein binding moieties having efficacious against disease. The method comprises, combining the protein binding moieties identified as efficacious against disease; testing the combination of protein binding moieties for efficacy against disease; identifying the synergistic combination of protein binding moieties.

When the present method is used to screen against one immunogen, the protein binding moieties comprising the synergistic combination may have synergistic efficacy because each protein binding moiety binds to a different epitope of the immunogen, or a protein binding moiety may bind to the immunogen and cause a conformational change, thus exposing an epitope that was otherwise not accessible, which is bound by another protein binding moiety. Synergism may also occur for any other reason known to one of skill in the art.

The combination of the protein binding moieties having synergistic efficacy may be used in manufacturing a pharmaceutical composition.

Another embodiment comprises a pharmaceutical composition, comprising the synergistic combination of protein binding moieties identified.

Another embodiment further comprises identifying the epitopes of the immunogen that are specifically bound by the synergistic combination of protein binding moieties; and combining the epitopes identified to form a multivalent vaccine.

Another embodiment comprises a vaccine, comprising the epitopes of the immunogen that are specifically bound by the synergistic combination of protein binding moieties identified.

An embodiment of the present invention exemplifies the methods for identifying antibodies or functional fragments thereof that inhibit the virulence of a pathogen, wherein said combination of antibodies or functional fragments thereof provides a synergistic ability to inhibit the virulence of said pathogen.

Screening Against Two or More Immunogens

Another embodiment comprises a method for identifying a therapeutic agent efficacious against disease, wherein the screening of a library of protein binding moieties comprises screening a library of protein binding moieties against two or more immunogens or a first and a second immunogen. In the present embodiment one library or a plurality of libraries can be used to screen against the immunogens.

The embodiment comprising screening against two or more immunogens or a first and a second immunogen can provide additional information as compared to screening against one immunogen. For example, once protein binding moieties efficacious against disease are identified than it can be determined which of the immunogens is an appropriate target for immunotherapy, or likewise which can be used as a vaccine.

Once appropriate target immunogens are identified, combinations of synergistic immunogens can be identified. In addition the protein binding moieties effective against disease can be combined and synergistic combinations of protein binding moieties that may bind to different immunogens can be identified. Once synergistic combinations of protein binding moieties are identified than their epitopes can be mapped and the epitopes can be manufactured to form synergistic multivalent vaccine.

An embodiment comprises a method for identifying protein binding moieties efficacious against disease, further comprising the steps of: (a) combining two or more of the pools of protein binding moieties, to form at least one mixture, wherein each mixture contains at least two protein binding moieties that are specific for different antigens; and (b) testing the mixtures for efficacy against disease.

The screening of two or more immunogens also increases the likelihood that protein binding moieties will be generated against the most efficacious immunogens or epitopes of immunogens for the treatment of disease.

A preferred embodiment further comprises combining the pluralities of protein binding moieties specific for the first immunogen with the plurality of protein binding moieties specific for the second immunogen; testing the combination of pluralities of protein binding moieties for efficacy against disease; and identifying the synergistic combination of pluralities of protein binding moieties efficacious against disease. Of note, when a library is screened against more than one immunogen, more than one plurality of protein binding moieties results, each plurality is specific for a unique immunogen. The pluralities each may comprise one, dozens, or more than a hundred protein binding moieties having relative specificity against an immunogen.

Another embodiment further comprises identifying the synergistic combination of immunogens relevant for the treatment of disease. As mentioned, once the synergistic combination of pluralities of protein binding moieties against more than one immunogen are identified than the appropriate target immunogens can be identified.

An embodiment of the present invention exemplifies a method for identifying protein binding moieties efficacious against disease, further comprising the steps of: (a) identifying the antigens used to generate the protein binding moiety mixtures that are efficacious against disease; (b) obtaining a plurality of protein binding moieties that are specific for the antigens of step (a); (c) dividing the plurality of protein binding moieties into at least a first pool and a second pool, wherein each pool contains one or more protein binding moieties, and wherein the protein binding moieties in their respective pool are testable with the other protein binding moieties within said pool; (d) testing said protein binding moieties from said first pool for efficacy against disease; (e) dividing the protein binding moieties from said first pool into two or more sub-pools, to the extent inhibition of virulence of said pathogen is observed in step (d), wherein each sub-pool contains one or more protein binding moieties; (f) testing said protein binding moieties from said first and second sub-pools of said first pool for efficacy against disease; and (g) identifying one or more protein binding moieties from step (f) that are efficacious against disease.

The present invention also provides that once the effective antigens are identified by testing the mixtures of protein binding moieties, then protein binding moieties can be identified that are generated by the antigens and are effective against disease, and these protein binding moieties can then be combined for therapy.

The present embodiment identifies protein binding moieties generated from each of these immunogens that are effective against disease.

Another embodiment further comprises manufacturing a pharmaceutical composition comprising the synergistic combination of pluralities of protein binding moieties identified as efficacious against disease.

Another embodiment comprises a pharmaceutical composition, comprising the synergistic combination of pluralities of protein binding moieties identified.

Another embodiment further comprises identifying the epitopes of the immunogens that are specifically bound by the synergistic combination of pluralities of protein binding moieties identified as efficacious against disease; and combining the epitopes identified to form a multivalent vaccine.

Another embodiment further comprises manufacturing a vaccine comprising the immunogens identified as relevant for the treatment of disease.

Another embodiment comprises a vaccine, comprising the epitopes of the immunogen that are specifically bound by the synergistic combination of pluralities of protein binding moieties identified.

Another embodiment comprises a vaccine, comprising the synergistic combination of immunogens identified.

An embodiment of the present invention comprises the protein binding moieties identified according to present invention for use as a therapy or passive immunization.

Isolation of Synergistic Immunogens for Production of a Vaccine or Protein Binding Moiety Another embodiment comprises combining a subset of the pluralities of protein binding moieties identified as a synergistic combination, wherein the subset combination comprises at least one less plurality of protein binding moieties than the synergistic combination; testing the subset combination of pluralities of protein binding moieties for efficacy against disease; identifying the subset combination of pluralities of protein binding moieties that maintains synergistic activity. Another embodiment further comprises identifying the subset combination of immunogens relevant for the treatment of disease.

For example, if more than one immunogen is screened and a synergistic combination of immunogens is identified, but it is not clear if each individual immunogen of the combination is necessary in order to maintain synergistic efficacy. In that instance, a subset of the protein binding moieties identified as a synergistic combination can be combined and tested and if the synergistic efficacy is maintained than a more cost effective vaccine can be manufactured using the subset combination of immunogens rather than the larger combination. See Example 6 below.

Another embodiment comprises a pharmaceutical composition, comprising the subset combination of pluralities of protein binding moieties that maintains synergistic activity.

Another embodiment comprises a vaccine, comprising the epitopes of the immunogen that are specifically bound by the subset combination of pluralities protein binding moieties that maintains synergistic activity.

Another embodiment comprises a vaccine, comprising the subset combination of immunogens identified.

Another embodiment comprises combining a subset of protein binding moieties identified as a synergistic combination, wherein the subset combination comprises at least one less protein binding moiety than the synergistic combination; testing the subset combination of protein binding moieties for efficacy against disease; identifying the subset combination of protein binding moieties that maintains synergistic activity. For example, if more than one immunogen is screened, a synergistic combination of immunogens is identified, and multiple protein binding moieties specific for each immunogen are identified to have efficacy against disease, as shown Example 7 below, then the present embodiment can be used to identify the minimum combination of protein binding moieties necessary to maintain synergistic efficacy against disease. This embodiment allows for the production of a cost effective combination therapy comprising protein binding moieties.

Another embodiment comprises manufacturing a pharmaceutical composition comprising the synergistic subset combination of protein binding moieties.

Another embodiment comprises identifying the epitopes of the immunogen that are specifically bound by the synergistic subset combination of protein binding moieties; and combining the epitopes identified to form a multivalent vaccine.

Another embodiment comprises a pharmaceutical composition, comprising the subset combination of protein binding moieties that maintains synergistic activity.

Another embodiment comprises a vaccine, comprising the epitopes of the immunogen that are specifically bound by the subset combination of protein binding moieties that maintains synergistic activity.

Vaccine Identification Without First Identifying the Protein Binding Moieties

Another embodiment comprises a method for identifying a vaccine comprising screening a library of protein binding moieties against a first and a second immunogen; obtaining a plurality of protein binding moieties that are specific for the first and second immunogens; combining the plurality of protein binding moieties specific for the first immunogen with the plurality of protein binding moieties specific for the second immunogen, testing the combination of pluralities of protein binding moieties for efficacy against disease; identifying the synergistic combination of pluralities of protein binding moieties efficacious against disease; identifying the synergistic combination immunogens relevant for the treatment of disease.

Another embodiment further comprises manufacturing a vaccine comprising the immunogens identified as relevant for the treatment of disease.

The following examples are intended to enable the methods of the claimed invention, however, are not intended to be limiting.

EXAMPLES

Example 1

Deconvolution after Screening Against One Immunogen

A library of protein binding moieties is screened against one immunogen. A plurality of protein binding moieties is obtained that are specific for the immunogen, where each member of the pool is defined and accessible. For example, if the library comprises a phage display library, then the protein binding moieties identified by the present invention will be linked to the DNA that encodes them; therefore, the sequence of the protein binding moieties is readily identifiable and the protein binding moieties can be reproduced easily.

The plurality of protein binding moieties specific for an immunogen may contain hundreds of moieties. Testing each of the individual moieties for efficacy against disease would be very time consuming, laborious and expensive. The plurality of protein binding moieties is divided into at least a first and a second pool, wherein each pool contains at least one protein binding moiety that is unique to that pool, and the protein binding moieties in their respective pool are testable with the other protein binding moieties within said pool. Protein binding moieties from the first pool are tested against disease, in order to determine efficacy. The disease can be an infectious disease, cancer, allergy or autoimmune disease. For example, if the disease to be treated is an infectious disease, the protein binding moieties are tested for functionality against the target pathogen. If the first pool fails to have efficacy against disease then study of the first pool will discontinue, thus, efficiently eliminating the protein binding moieties from the first pool as potential therapeutic candidates. If efficacy against disease is observed then the first pool can be sub-divided into at least a first and a second sub-pool, wherein each sub-pool contains at least one protein binding moiety. The first and second sub-pools are then tested for efficacy against disease. The sub-pools containing binders effective against disease are identified. The sub-pools may be further subdivided and the sub-sub-pools are then tested for efficacy against disease until individual protein binding moieties having efficacy against disease are identified. This method is an efficient method for identifying binders effective against disease without first sequencing each of the moieties specific for the immunogen or having to test each individually.

The second pool identified by the screening against the immunogen may be tested against a disease in order to determine efficacy against said disease. If efficacy against disease is observed then the second pool can be sub-divided into at least a first and a second sub-pool, wherein each sub-pool contains at least one protein binding moiety. The first and second sub-pools are then tested for efficacy against disease. The sub-pools containing binders effective against disease are identified. The sub-pools may be further subdivided and the sub-sub-pools are then tested for efficacy against disease until individual protein binding moieties having efficacy against disease are identified.

Example 2

Identification of Synergistic Protein Binding Moieties

More than one protein binding moiety having efficacy against disease may be identified. These functional binders may then be combined in order to identify a synergistic or non-synergistic combination for treatment. For example, if functional protein binding moieties X, Y, and Z are identified. Then the combinations of XY, XZ, YZ, and XYZ can be formed. Each combination is tested for efficacy against disease. A synergistic combination may be the combination of protein binding moieties whose efficacy is greater than the sum of their individual protein binding moieties' efficacies. Synergism may be explained by the ability of different binders to bind to different epitopes of the target. The binding of one epitope may provide that the binding to another epitope by another protein binding moieties may result in a more efficacious result than the binding to a single epitope.

Example 3

Generation of a Multivalent Vaccine

In addition, if more than one functional protein binding moieties is identified, the epitopes of the functional binders can be mapped by methods known to one of skill in the art. Once the epitopes are identified, the epitopes can be reproduced and combined in order to form a multivalent vaccine.

Example 4

Identification of Therapeutically Relevant Immunogens

A library of protein binding moieties is screened against more than one immunogen. For example, the library is screened against immunogens A, B, C and D. Four individual screenings may be completed, where a library is screened against one immunogen. In this example, four pluralities of protein binding moieties are generated that are specific for one immunogen, A, B, C or D, respectively. The pluralities are used as the source of protein binding moieties specific for A, B, C, and D in the following methods.

Optionally, the pluralities of protein binding moieties specific to immunogens, A, B, C or D, are individually tested for efficacy against disease. From this step the immunogens, which are potential therapeutic targets and which can be used as potential efficacious vaccines, are determined. Once the efficacious immunogens are identified then vaccines incorporating each of the efficacious immunogens can be generated by methods known in the art.

Example 5

Identification of Synergistic Immunogens

The purpose of the next steps is to identify synergistic combinations of immunogens, which can be used as vaccines and/or which in combination are potential therapeutic targets. The pools of protein binding moieties specific to A, B, C or D are combined in at least the following combinations: AB, AC, AD, BC, BD, CD, ABC, BCD and ABCD. Each of the combinations is then tested to determine efficacy against disease. From this step the synergistic combinations of immunogens, which are potential therapeutic targets and which can be used as potential efficacious vaccines, are determined.

Example 6

Isolation of Synergistic Immunogens

If for example, the combination of protein binding moieties specific to ABC is found to have synergistic effective against disease and it is not clear which of the specific immunogens is efficacious, the following steps could be completed. The protein binding moieties specific to AB should be tested to determine efficacy against disease and the results should be compared to the results of the ABC test to determine if C is an efficacious target or synergistic component of a potential vaccine. If the protein binding moieties specific to AB were already tested then the results of the AB test can be compared to the results of the ABC test to determine if C is an efficacious target or synergistic component of a potential vaccine. Then protein binding moieties specific to A should be tested alone to determine efficacy against disease and the results compared to the results of the AB test to determine if B is an efficacious target or component of a potential vaccine. If the protein binding moieties specific to A were already tested then the results of the A test can be compared to the results of the AB test to determine if B is also an efficacious target or component of a potential vaccine.

Once the synergistic combinations of immunogens are identified than efficacious vaccines incorporating the synergistic combinations immunogens can be generated by methods known in the art.

The above methods can be used when the immunogens are distinct immunogens or when the immunogens are different epitopes of the same immunogen. For further clarification, in the above example, A, B, C and D could represent different immunogens or different epitopes of the same immunogen.

Example 7

Deconvolution after Screening Against More than One Immunogen

The purpose of the next steps is to identify a synergistic combination or combinations of protein binding moieties for the treatment of disease. From the methods described above, the target immunogens having synergistic effects are identified. For example, immunogens A, B and C are identified as targets having synergistic efficacy. The next step is to identify the protein binding moieties having efficacy against a specific immunogen. The methods of Example 1 are utilized to identify each of the protein binding moieties having efficacy against the specific immunogens A, B, C. For example from the methods of Example 1, three protein binding moieties are identified that are efficacious against each of the immunogens A, B, C. For this example, they will be identified as A1, A2, A3, B1, B2, B3, C1, C2, and C3. In order to identify the most efficacious combination, a process of elimination is followed. For comparison an test is completed using the combination of the protein binding moieties A1, A2, A3, B1, B2, B3, C1, C2, and C3. This will act as a reference point. Then a test is completed using the combination of the protein binding moieties A1, A2, A3, B1, B2, B3, C1, and C2. If the efficacy is the same as the combination of all of the efficacious protein binding moieties specific to A, B and C, then C3 can be eliminated as a potential candidate. Following the process of elimination, a test is completed using the combination of the protein binding moieties A1, A2, A3, B1, B2, B3, C1. If the efficacy is the same as the combination of all of the efficacious protein binding moieties specific to A, B and C, then C2 can be eliminated as a potential candidate and it can be determined that C1 is the best choice of protein binding moieties specific to C for synergistic combination therapy.

In order to determine the best protein binding moiety specific to B then a test is completed using the combination of the protein binding moieties A1, A2, A3, B1, B2, C1, C2 and C3. If the efficacy is the same as the combination of all of the efficacious protein binding moieties specific to A, B and C, then B3 can be eliminated as a potential candidate. Following the process of elimination, a test is completed using the combination of the protein binding moieties A1, A2, A3, B1, C1, C2 and C3. If the efficacy is the same as the combination of all of the efficacious protein binding moieties specific to A, B and C, then B2 can be eliminated as a potential candidate and it can be determined that B1 is the best choice of protein binding moieties specific to B for synergistic combination therapy.

In order to determine the best protein binding moiety specific to A then an test is completed using the combination of the protein binding moieties A1, A2, B1, B2, B3, C1, C2 and C3. If the efficacy is the same as the combination of all of the efficacious protein binding moieties specific to A, B and C, then A3 can be eliminated as a potential candidate. Following the process of elimination, an test is completed using the combination of the protein binding moieties A1, B1, B2, B3, C1, C2 and C3. If the efficacy is the same as the combination of all of the efficacious protein binding moieties specific to A, B and C, then A2 can be eliminated as a potential candidate and it can be determined that A1 is the best choice of protein binding moieties specific to A for synergistic combination therapy. Following this example, then the best synergistic combination of protein binding moieties would be A1, B1, and C1. A1, B1, and C1 are then combined by methods known in the art to generate an effective combination therapy.

The invention claimed is:

1. A method for identifying an antibody or antigen binding fragment thereof comprising the steps of:

(a) screening a library of antibodies or antigen binding fragments against at least one immunogen;

(b) obtaining a plurality of antibodies or antigen binding fragments that are specific for the immunogen;

(c) dividing the plurality of antibodies or antigen binding fragments into at least a first pool and a second pool, wherein each pool contains at least one antibody or antigen binding fragment;

(d) testing said antibodies or antigen binding fragments from said first pool for function in an vitro assay;

(e) dividing the antibodies or antigen binding fragments from said first pool into two or more sub-pools, to the extent function in an vitro assay is observed in step (d), wherein each sub-pool contains at least one antibody or antigen binding fragment;

(f) testing said antibodies or antigen binding fragments from said first and second sub-pools of said first pool for function in an vitro assay; and (g) identifying at least one antibody or antigen binding fragment from step (f) that are functional in an vitro assay.

2. A method according to claim 1, further comprising:

(h) testing said antibodies or antigen binding fragments from said second pool for function in an vitro assay;

(i) dividing the antibodies or antigen binding fragments from said second pool into two or more sub-pools, to the extent function in an vitro assay is observed in step (h), wherein each sub-pool contains at least one antibody or antigen binding fragment;

(j) testing said antibodies or antigen binding fragments from said first and second sub-pools of said second pool for function in an vitro assay efficacy against disease; and (k) identifying at least one antibody or antigen binding fragment from step (j) that is functional in an vitro assay.

3. The method according to claim 1, wherein the library of antibodies or antigen binding fragments used to screen against at least one immunogen comprises a phage display library displaying antibodies or antigen binding fragments thereof.

4. The method according to claim 1, further comprising:

(h) combining the antibodies or antigen binding fragments identified as functional in an vitro assay;

(i) testing the combination of antibodies or antigen binding fragments for function in an vitro assay; and (j) identifying a synergistic combination of antibodies or antigen binding fragments.

5. The method according to claim 4, further comprising:

(k) combining a subset of the antibodies or antigen binding fragments identified as a synergistic combination, wherein the subset combination comprises at least one less antibody or antigen binding fragment than the synergistic combination;

(l) testing the subset combination of antibodies or antigen binding fragments for function in an vitro assay; and (m) identifying the subset combination of antibodies or antigen binding fragments that maintains synergistic activity.

6. The method according to claim 1, wherein step (a), the screening of a library of antibodies or antigen binding fragments comprises screening a library of antibodies or antigen binding fragments against a first and a second immunogen.

7. The method according to claim 6, wherein step (b) of claim 1, the obtaining a plurality of antibodies or antigen binding fragments that are specific for the immunogen, further comprises:

(ba) combining the plurality of antibodies or antigen binding fragments specific for the first immunogen with the plurality of antibodies or antigen binding fragments specific for the second immunogen;

(bb) testing the combination of pluralities of antibodies or antigen binding fragments for function in an vitro assay; and (be) identifying a synergistic combination of pluralities of antibodies or antigen binding fragments functional in an vitro assay.

8. The method according to claim 7, further comprising:

(bd) combining a subset of the pluralities of antibodies or antigen binding fragments identified as a synergistic combination, wherein the subset combination comprises at least one less antibody or antigen binding fragment than the synergistic combination;

(be) testing the subset combination of pluralities of antibodies or antigen binding fragments for function in an vitro assay; and (bf) identifying the subset combination of pluralities of antibodies or antigen binding fragments that maintains synergistic activity.

* * * * *